(12) United States Patent
Niblett

(10) Patent No.: US 6,869,761 B1
(45) Date of Patent: Mar. 22, 2005

(54) DETECTION AND DIFFERENTIATION OF SPECIFIC STRAINS OF CITRUS TRISTEZA VIRUS

(76) Inventor: Charles Niblett, 822 SW. 50$^{th}$ Way, Gainesville, FL (US) 32607

(*) Notice: Subject to any disclaimer, the term of this patent is extended or adjusted under 35 U.S.C. 154(b) by 355 days.

(21) Appl. No.: 09/652,941

(22) Filed: Aug. 31, 2000

Related U.S. Application Data

(63) Continuation-in-part of application No. 08/904,290, filed on Jul. 31, 1997, now Pat. No. 6,140,046.

(51) Int. Cl.$^7$ .......................... C12Q 1/68; C12P 19/34; C07H 21/04
(52) U.S. Cl. ...................... 435/6; 435/91.1; 435/91.2; 536/23.1; 536/24.3
(58) Field of Search .................... 435/6, 91.1, 91.2; 536/23.1, 24.3

(56) References Cited

U.S. PATENT DOCUMENTS

| | | | |
|---|---|---|---|
| 5,344,952 A | * 9/1994 | Mize et al. | 558/169 |
| 5,426,026 A | 6/1995 | Jordan | |
| 5,593,836 A | * 1/1997 | Niemiec et al. | 435/6 |
| 6,017,699 A | 1/2000 | Jordan | |
| 6,037,124 A | * 3/2000 | Matson | 435/6 |
| 6,140,046 A | * 10/2000 | Niblett | 435/6 |

OTHER PUBLICATIONS

H Pappu et al., Virus Genes,"Comparative Sequence Analysis of the Coat Proteins of Biologically Distinct Citrus Tristeza Closterovirus Isolates," 1993, 7:3, pp. 255–264.*

M Mawassi et al., Virus Genes, "Nucleotide Sequence of the Coat Protein Gene of Citrus Tristeza Virus:Comparison of Biologically Diverse Isolates Collected in Israel," 7:3, 265–275.*

B Cevik et al., "Detection and differentiation of strains of citrus tristeza closterovirus using a point mutation and minor sequence differences in their coat protein genes," 1996, vol. 86, No. 11, Abstract Only.*

Nolasco et al., "Sensitive CTV diagnosis using immunocapture, reverse transcriptional polymerase chain reaction and an exonuclease flourescent probe assay," Fruits, 52: 391–396, 1997.

Rowhani, et al., "Development of a Sensitive Colorimetric–PCR Assay for Detection of Viruses in Woody Plants," Plant Disease, 82: 880–884, 1998.

Schmid M. and G. Schalasta, "A Rapid and Reliable PCR Based Method for Detecting the Blood Coagulation Factor V Leiden Mutation," Biochemica, 3: 12–15, 1997.

Roche Molecular Biochemicals, 2000 Biochemicals Catalog, "PCR ELISA".

* cited by examiner

*Primary Examiner*—Jehanne Sitton
(74) *Attorney, Agent, or Firm*—Akerman Senterfitt

(57) ABSTRACT

Nucleic acid probes for detecting different strains of Citrus Tristeza Virus (CTV) were made and shown to be highly sensitive, specific, and selective. The invention also concerns a method of detection, a method of identifying novel strains of CTV, and a detection kit which employs the subject probes.

6 Claims, No Drawings

DETECTION AND DIFFERENTIATION OF SPECIFIC STRAINS OF CITRUS TRISTEZA VIRUS

CROSS-REFERENCE TO RELATED APPLICATIONS

The present application is a continuation-in-part of U.S. patent application Ser. No. 08/904,290 filed on Jul. 31, 1997, now U.S. Pat. No. 6,140,046.

STATEMENT REGARDING FEDERALLY SPONSORED RESEARCH OR DEVELOPMENT

Not applicable.

BACKGROUND OF THE INVENTION

Citrus Tristeza Virus (CTV) is a serious pathogen in most citrus producing regions of the world. It has the largest RNA genome of any plant virus known. There are many known strains of CTV, each of which can cause a variety of symptoms in different host species. These known strains of CTV have been categorized into five major groups based on their biological activity. These groups are commonly known as: mild; seedling yellows (SY); decline on sour orange (QD); stem pitting on grapefruit (SP-G); and stem pitting on sweet orange (SP-0) (Garnsey, S. M., Barrett, H. C., and Hutchison, D. J., 1987. "Identification of citrus tristeza virus resistance in citrus relatives and potential applications." *Phytophylactica* 19:187–197). The symptoms caused by the different strains of CTV can range from insignificant, to disfiguring, to severe damage even of mature trees. Mild strains cause no symptoms on most commercial and commonly grown citrus varieties; whereas the strains in the other four categories cause severe effects including, for example, death of the host citrus trees.

Such a great diversity of symptoms caused by CTV requires techniques to detect and differentiate these strains if CTV is to be controlled. Recognizing this need, the State of Florida, which benefits greatly from the citrus industry, implemented the Quality Tree Program of Florida, which mandates frequent testing of thousands of citrus propagation trees for the presence of severe strains of CTV. Symptoms development on differential indicator hosts (McClean et al., 1977, Gamsey, supra) and aphid transmissibility (Roistacher, C. N. and Bar-Joseph, M., 1984. "Transmission of tristeza and seedling yellows tristeza by small population of Aphis gossypii." *Plant Disease* 68:494–496) were used for this purpose in the past. Since these methods were costly and time consuming, other techniques such as cDNA probe hybridization (Rosener. A., Lee, R. F., and Bar-Joseph, M. 1986. "Differential hybridization with cloned cDNA sequences for detecting a specific strain of citrus tristeza virus." *Phytopathology* 76:820–824), dsRNA analysis (Dodds, J. A., R. J. Jordan, Roistacher, C. N., and T. Jarupat. 1987. "Diversity of citrus tristeza virus isolates indicated by dsRNA analysis." *Intervirology* 27:177–188), polypeptide map analysis (Guerri, J., Moreno, P., and Lee R. F. 1990. "Identification of citrus tristeza virus strains by peptide maps of virion coat protein." *Phytopathology* 80:692–698) and RFLP analysis (Gillings et al., 1993; Akbulut, 1995) were developed. Hybridization using nucleic acid probes, either radioactively or nonradioactively labeled, has been used for detection and/or differentiation of many plant pathogens, including the viruses CTV (Rosner, supra), potato virus Y (Singh et al 1995), geminiv ruses (Gilbertson et al., 1991) luteoviruses (Martin et al., 1990) and insect transmitted viruses (Harper and Creamer 1995). Although these methods enabled differentiation of certain strains of CTV, they are not adaptable to rapid large scale assays.

As an alternative to these methods, a monoclonal antibody, MCA13, was developed, which reacts prodominantly with most severe strains, but not with mild strains of CTV (Permar, T. A., Garnsey, S. M., Gumpf, D. J., and Lee, R. L. 1990. "A monoclonal antibody that discriminate strains of citrus tristeza virus." *Phytopathology* 80:224–228). The current method of analysis for the presence or absence of CTV employs MCA13 in an enzyme-linked immunosorbent assay (ELISA) which has the advantage of being scaled up to process large numbers of samples at a relatively low cost. It has been determined that the MCA13 binds to a particular epitope of the capsid protein of CTV. Although the ELISA method using MCA13 is sensitive and reliable, it can only differentiate between mild and severe strains of CTV. There currently is no method available to differentiate between and amongst the mild and severe strains such as QD, SP-0, and SP-G.

Accordingly, a nucleic acid probe which can differentiate between the severity of symptoms caused by strains of CTV in plants is highly desirable as a diagnostic tool for detecting the potential problems of CTV infection in a plant. In addition, a nucleic acid probe having a further advantage of being capable of being scaled up to process large numbers of samples would be beneficial to programs such as the Florida Quality Tree Program, and the citrus industry as a whole.

BRIEF SUMMARY OF THE INVENTION

The present invention is summarized in that a method to assay for the symptom severity of a strain of plant pathogenic virus is based on nucleotide sequence heterogeneity of the strains of the virus. The heterogeneous nucleotide sequence used does not have to be related etiologically to the differences in symptom severity. As shown in the example described below, an association between symptom severity and nucleotide sequence of a capsid protein gene is sufficient to enable the design of a DNA based assay for viral symptom severity.

The gene sequences encoding the CTV capsid protein from a number of biologically and geographically distinct strains of CTV have been determined. Nucleotide sequence differences of capsid protein genes (CPGs) of a number of CTV strains were discovered to be associated with the types of symptoms caused by the strains. Even though the CPG sequences of various CTV strains have a high degree of identity, differences of 1–10% were found in the nucleotide sequences. (Pappu, H. R., Pappu, S. S., Manjunath, K. L., Lee R. F., and Niblett, C. L. 1993. "Molecular characterization of a structural epitope that is largely conserved among severe isolates of a plant virus." *Proc. Natl. Acad. Sci. USA* 90:3641–3644; and Akbulut, supra).

These differences in nucleic acid sequences were exploited to develop group-specific oligonucleotide probes useful for differentiation between and among strains of CTV. Seven different probes, each specific for one of seven biologically distinct groups of CTV strains, a general probe specific for all mild strains of CTV (capable of differentiating those from severe strains of CTV), and a universal probe for specifically detecting all strains of CTV, were made. Hybridization of the novel probes with 14 different strains of CTV representing each of seven biologically distinct groups showed that these probes are able to clearly differentiate all known groups of CTV strains. Thus, it is a specific object of the subject invention to provide a nucleic acid probe which is capable of rapid identification and classification of known or newly discovered CTV isolates.

Advantageously, the subject probes can be used to process large numbers of samples at a relatively inexpensive cost. A further advantage of the oligonucleotide probes of the subject invention is that they can be labeled with biotin, which can provide increased sensitivity, a long shelf life, the capability of repeated use for an extended period of time, a decreased health hazard as compared to radioactive labels, and the like.

It is another object of the invention to provide a method for detecting CTV infection in a host plant by employing an oligonucleotide probe as described herein. The method comprises isolation of genetic material from a suspected pathogen (a CTV strain) which can be present in a host, or a sample taken from a host, conducting standard hybridization procedures on the isolated genetic material using one or more polynucleotide probe of the invention, and determining the presence or absence of the pathogen in the host based on a positive or negative reaction of the hybridization. The probes and method of the subject invention can thus be used as a reliable, specific, and cost-effective diagnostic procedure in the control of CTV in citrus plants.

A further object of the invention includes identifying novel strains of CTV by employing certain of the subject probes.

It is yet another object of the subject invention to provide a kit for carrying out the method of the subject invention. The kit can comprise a probe, or mixture of probes, for hybridizing with genetic material isolated for use with the kit. The kit can also include materials necessary for isolating CTV genetic material, labeling of the probes, or performing the hybridization assay.

Unless otherwise defined, all technical terms used herein have the same meaning as commonly understood by one of ordinary skill in the art to which this invention belongs. Commonly understood definitions of molecular biology terms can be found in Rieger et al., Glossary of Genetics: Classical and Molecular, 5th edition, Springer-Verlag: New York, 1991; and Lewin, Genes V, Oxford University Press: New York, 1994.

By "gene," "coding sequence," or a "nucleic acid that encodes" a particular polypeptide is generally meant a nucleic acid molecule that is transcribed (in the case of DNA) and translated (in the case of mRNA) into the polypeptide in vitro or in vivo when placed under the control of appropriate regulatory sequences.

As used herein, a "nucleic acid," "nucleic acid molecule," "oligonucleotide," or "polynucleotide" means a chain of two or more nucleotides such as RNA (ribonucleic acid) and DNA (deoxyribonucleic acid). A "purified" or "isolated" nucleic acid molecule is one that has been substantially separated or isolated away from other nucleic acid sequences in a cell or organism in which the nucleic acid naturally occurs (e.g., 30, 40, 50, 60, 70, 80, 90, 95, 96, 97, 98, 99, 100% free of contaminants). The term includes, e.g., a recombinant nucleic acid molecule incorporated into a vector, a plasmid, a virus, or a genome of a prokaryote or eukaryote. Examples of purified nucleic acids include cDNAs, fragments of genomic nucleic acids, nucleic acids produced polymerase chain reaction (PCR), nucleic acids formed by restriction enzyme treatment of genomic nucleic acids, recombinant nucleic acids, and chemically synthesized nucleic acid molecules. The phrase "isolating a nucleic acid" includes using PCR to amplify the nucleic acid from a test sample.

When referring to hybridization of one nucleic to another, "low stringency conditions" means in 10% formamide, 5× Denhart's solution, 6× SSPE, 0.2% SDS at 42° C., followed by washing in 1× SSPE, 0.2% SDS, at 50° C.; "moderate stringency conditions" means in 50% formamide, 5× Denhart's solution, 5× SSPE, 0.2% SDS at 42° C., followed by washing in 0.2× SSPE, 0.2% SDS, at 65° C.; and "high stringency conditions" means in 50% formamide, 5× Denhart's solution, 5× SSPE, 0.2% SDS at 42° C., followed by washing in 0.1× SSPE, and 0.1% SDS at 65° C. The phrase "stringent hybridization conditions" means low, moderate, or high stringency conditions as well as the hybridization conditions described in Example 1 below.

The term "labeled," with regard to a probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using an enzyme-conjugated secondary antibody and end-labeling of a DNA probe with biotin such that it can be detected with enzyme-conjugated streptavidin.

By the term "immobilized" is meant attached to with high affinity. For example, a nucleic acid is immobilized when it is covalently bonded to a blotting substrate (e.g., a nylon membrane) or a microtiter plate (e.g., to the bottom wells in a polystyrene microtiter plate). Nucleic acids can also be immobilized to a substrate by strong non-covalent bonding, e.g., such that the nucleic acids remain attached to the substrate under stringent hybridization conditions or after washing in an ELISA (enzyme-linked immunosorbent assay) protocol (see Examples section below).

As used herein, the term "antibody" includes whole immunoglobulin as well as immunoglobulin fragments such as $F(ab')_2$ fragments, Fab fragments, or any other like molecule derived from an immunoglobulin and having a region that binds to a particular antigen, including proteolytic fragments of an immunoglobulin or genetically engineered molecules.

Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions will control. In addition, the particular embodiments discussed below are illustrative only and not intended to be limiting.

BRIEF DESCRIPTION OF THE SEVERAL VIEWS OF THE DRAWINGS

Not applicable.

DETAILED DESCRIPTION OF THE INVENTION

The present invention describes the design of a DNA-based test for symptom severity of strains of a plant pathogenic virus. It is demonstrated here that it is possible to analyze the variations in nucleotide sequence among strains of a pathogenic virus and draw associations between specific sequences and levels or severity of symptoms seen in plants infected with differing strains. The differences in nucleotide sequence need not be related to differences in disease ethiology. In the examples shown below, the variable genetic region is in the gene encoding the viral capsid protein and such variations are presumably not related directly to symptom severity differences in infected plants. However by analyzing differences in nucleotide sequence and differences in symptom severity, it is possible to find nucleotide sequences which correlate well with symptom severity. Once such diagnostic DNA sequences are identified, it then becomes possible to design hybridizing DNA probes which will selectively bind only to nucleic acids from viruses having a pre-determined level of symptom severity. As shown in the example here, this method can be used with an RNA virus as well as with DNA viruses. For RNA viruses, it is convenient if the targeted portion of the viral genome is first reverse transcribed to DNA, as is described below.

Biological Methods

Methods involving conventional molecular biology techniques are described herein. Such techniques are generally known in the art and are described in detail in methodology treatises such as Molecular Cloning: A Laboratory Manual, 2nd ed., vol. 1–3, ed. Sambrook et al., Cold Spring Harbor Laboratory Press, Cold Spring Harbor, N.Y., 1989; and Current Protocols in Molecular Biology, ed. Ausubel et al., Greene Publishing and Wiley-Interscience, New York, 1992 (with periodic updates). Various techniques using polymerase chain reaction (PCR), including reverse transcriptase PCR (RT-PCR), are described, e.g., in Innis et al., PCR Protocols: A Guide to Methods and Applications, Academic Press: San Diego, 1990. Methods for chemical synthesis of nucleic acids are discussed, for example, in Beaucage and Carruthers, Tetra. Letts. 22:1859–1862, 1981, and Matteucci et al., J. Am. Chem. Soc. 103:3185, 1981. Chemical synthesis of nucleic acids can be performed, for example, on commercial automated oligonucleotide synthesizers. Immunological methods (e.g., preparation of antigen-specific antibodies, immunoprecipitation, and immunoblotting) are described, e.g., in Current Protocols in Immunology, ed. Coligan et al., John Wiley & Sons, New York, 1991; and Methods of Immunological Analysis, ed. Masseyeff et al., John Wiley & Sons, New York, 1992.

Detection and Differentiation of CTV Strains

The subject invention concerns novel diagnostic tools for detecting the presence or absence of Citrus Tristeza Virus (CTV). Described here are novel nucleic acid probes which can hybridize specifically and selectively (e.g., stringent hybridization conditions) to diagnostic sequences from strains of CTV which are associated with a level of CTV symptom severity in infected plants. In a preferred embodiment, the subject invention comprises a polynucleotide which hybridizes selectively and specifically to a segment of a capsid protein (CPG) gene of CTV, wherein the CPG segment is unique to a CTV strain in Group I, Group II, Group III, Group IV, Group V, Group VI, or Group VII. The probes of the subject invention which hybridize to these CTV groups are designated as Probe I (SEQ. ID. NO. 1), Probe II (SEQ. ID. NO. 2), Probe III (SEQ. ID. NO. 3), Probe IV (SEQ. ID. NO. 4), Probe V (SEQ. ID. NO. 5), Probe VI (SEQ. ID. NO. 6), and Probe VII (SEQ. ID. NO. 7), respectively.

The classification of the CTV strains in Groups I–VII is based on biological similarities, mainly symptom type and severity. That grouping is not related to the choice of the portion of the CTV genome to analyze for genetic variability. Instead, a region of the CTV genome known to be variable, the capsid protein gene (CPG) was used. The groupings of the viral strains based on symptom severity are shown in Table 1 below:

TABLE 1

Properties of the CTV isolates whose CPG sequences were used for design of CTV group specific probes. The isolates whose amplified CPGs were used in Southern blot hybridization are highlighted.

| Group | Isolates | Symptoms[a] | Origin | Reference |
|---|---|---|---|---|
| I | T36 | QD + SY | Florida | Pappu et al., 1993 |
| | T66 | QD + SY | Florida | Pappu et al., 1993 |
| | 202B-1 | QD + SY + SP-G | Florida | |
| | T10 | QD+ | Florida | |
| | PB53DRF1 | SP-G | Australia | M. Gillings (personal communication) |
| II | B3 | SP-O | Japan | Pappu et al., 1993 |
| | Cu17b | SP | Cuba | V. J. Febres (personal communication) |
| | TR5 | NA | Turkey | Akbulut et at., 1995 |
| | TR12 | NA | Turkey | Akbulut et al., 1995 |
| | PB163BRF1 | SP-O + SY | Australia | M. Gillings (personal communication) |
| | B1BRF6 | SP-O + SY | Reunion | M. Gillings (personal communication) |
| | B30ARF1 | SP + SY | Japan | M. Gillings (personal communication) |
| | PB235BRF1 | SP-O + SY | Australia | M. Gillings (personal communication) |
| | PB192DRF1 | SP-O + SY | Australia | M. Gillings (personal communication) |
| III | B165 | SP-O + SP-G +QD | India | Manjunath et al., 1993 |
| | B185 | SP-O + SP-G + QD + SY | Japan | Pappu et al., 1993 |
| | B7 | SP-G + SY | South Africa | Pappu et al., 1993 |
| | S23 | Severe | Spain | |
| | S27 | Severe | Spain | |
| | PB219ERF5 | SP-G + QD | Australia | M. Gillings (personal communication) |
| IV | T3 | QD + SY | Florida | Pappu et al., 1993 |
| | B220 | SP-O + SP-G + QD | India | Manjunath et al., 1993 |
| | B227 | SP-O + SP-G + QD | India | Manjunath et al., 1993 |
| | B16ARF4 | SY + SP? | Brazil | M. Gillings (personal communication) |
| | PB61ERF5 | SY | Australia | M. Gillings (personal communication) |
| V | B128 | SP-O + SP-G | Colombia | Pappu et al., 1993 |
| | B249 | SP-O + SP-G | Venezuela | V. J. Febres (personal communication) |
| | FL7 | SP-G | Florida | |
| | FL15 | SP-G | Florida | |
| | PB219JRF1 | SP-G | Australia | M. Gillings (personal communication) |

TABLE 1-continued

Properties of the CTV isolates whose CPG sequences were used for design of CTV group specific probes. The isolates whose amplified CPGs were used in Southern blot hybridization are highlighted.

| Group | Isolates | Symptoms[a] | Origin | Reference |
|---|---|---|---|---|
| VI | T30 | Mild | Florida | Pappu et al., 1993 |
| | T26 | Mild | Florida | Pappu et al., 1993 |
| | T55 | Mild | Florida | Pappu et al., 1993 |
| | T4 | Mild | Florida | Pappu et al., 1993 |
| | 203C | Mild | Florida | |
| | 204D | Mild | Florida | |
| VII | B188 | Mild | Japan | Pappu et al., 1993 |
| | B213 | Mild | Korea | Pappu et al., 1993 |
| | B215 | Mild | Japan | Pappu et al., 1993 |

[a]Symptoms observed in the field trees or in greenhouse indicator plants:
QD = decline to scions grafted on sour orange rootstock;
SP-G = stem pitting on grapefruit scions;
SP-O = stem pitting on sweet orange scions;
SY = seedling yellows when indexed on sour orange seedlings;
Mild = symptoms on Mexican lime only.

Another embodiment of the invention comprises a polynucleotide useful as a probe which hybridizes specifically to (e.g., under stringent hybridization conditions), and is selective for, mild strains of CTV to the exception of severe strains of CTV. This probe is designated as Probe VIII (SEQ. ID. NO. 8). In yet another embodiment of the invention, the subject invention comprises a polynucleotide useful as a probe for specifically hybridizing to all strains of CTV, which is selective against pathogens which are not CTV. This probe is designated for purposes of the subject invention as Probe 0 (SEQ. ID. NO. 9). This probe is, in effect, a positive control for the presence of CTV.

of probes, taken as a whole, is capable of use as a probe panel to identify the likely symptom severity of a given CTV isolate.

It is to be understood that the DNA sequences presented in Table 2 below are probably not related biochemically to the differences in severity of symptoms caused by the CTV strains, but that is not important here. What is important is that these DNA sequences have been associated with a given level of severity of symptoms caused by strains of CTV and are thus diagnostic sequences of symptom severity.

Also presented in Table 2 below are the oligonucleotide primers used for RT/PCR amplification of the CTV CPG.

TABLE 2

| Probes | Sequence | Tm (° C.)[a] | Position[b] | CTV strains group[c] |
|---|---|---|---|---|
| Probe I | 5'GAAATACCGCACACAAGT-3' | 50 | 521–537 | Group I |
| Probe II | 5'TGACGCACGTCATTCAT-3' | 50 | 124–141 | Group II |
| Probe III | 5'CCACTTCGACGCCCT-3' | 50 | 323–337 | Group III |
| Probe IV | 5'TCCCGAGTATATGTTAT-3' | 46 | 307–323 | Group IV |
| Probe V | 5'ACACCCGTGGTATCATCGT-3' | 58 | 287–306 | Group V |
| Probe VI | 5'CCGCTAATCGGTATA-3' | 44 | 251–265 | Group VI |
| Probe VII | 5'CTGCACACAGATAATGA-3' | 48 | 515–531 | Group VII |
| Probe VIII | 5'TTATACACGATGTCGGT-3' | 48 | 358–374 | Mild strains |
| Probe 0 | 5'GGATCGATGTGTAA-3' | 40 | 97–100 | All strains |
| CN 119 | 5'AGATCTACCATGGACGACGAAACAAAG 3' | 52 | (−)9–18 | All strains |
| CN 120 | 5'GAATTCGCGGCCGCTCAACGTGTGTTA-3 | 54 | 653–(+)14 | All strains |

[a]Melting point temperatures (Tm) calculated using the following equation; Tm = 4 × (number of G and C) + 2 × (number of A and T).
[b]The location of the probe in the CPG nucleotide sequence.
[c]Group of CTV isolates to which the corresponding probe is specific.

In order to make the probes of the subject invention, coat protein gene sequences of 75 biologically and geographically distinct isolates of CTV were compared using the Clustal V sequence alignment computer program. Differences in the nucleotide sequences of these isolates were determined. Those isolates having the same differences in the same position of their nucleotide sequence were grouped together. A set of DNA probes were then designed based on this data as correlated with the grouping of strains for symptom severity. For each symptom severity group, a single probe was designed which would hybridize to DNA transcribed from strains of that severity group. Thus the set The primers CN119 and CN120 are also shown as SEQ. ID. NOS. 10 and 11, respectively.

The group specific oligonucleotide probe having a sequence complementary to the positive sense strand of the identified fragment can be made by techniques well known in the art. The subject probes were synthesized using commercially available synthesis apparatus in the DNA Synthesis Core of the Interdisciplinary Center for Biotechnology Research at the University of Florida. The probes of the subject invention can be labeled by any of the standard nucleic acid probe labeling techniques. These include radioactive and non-radioactive (e.g., enzymatic) labeling methods.

Using the nucleotide sequence differences found in the CPGs of a number of biologically and geographically different strains of CTV, the group specific oligonucleotide probes useful for differentiation of CTV strains were labeled with biotin. Biotin was used as an easily detectable marker, but other tags or markers which can be attached to DNA could have been used as well. A biotin molecule for non-radioactive detection was incorporated at the 5' ends of each of the subject probes during synthesis according to standard procedures. These probes were used to develop a non-radioactive blot hybridization method to differentiate the CTV strain groups. In a preferred embodiment, the subject probes are used in a "dot-blot" hybridization employing a nylon membrane. Dot-blot hybridization can be conducted using commercially available processes, apparatus, or kits, following the manufacturer's directions. For example, the dot-blot apparatus available from BIO-RAD Laboratories can be used. In a most preferred embodiment, the dot-blot procedure is conducted by stringent washing of the membranes just below the determined melting temperature of the probe. The melting temperature is dependent on the nucleotide composition of the sequence. Melting temperatures for the nucleotide sequences of the subject invention are provided in Table 2 above. Other methods for carrying out hybridization of the probes to a target sequence, as recognized by persons of ordinary skill in the art, are readily available for use with the subject probes.

Using a marker or label on the DNA probe, such as biotin, the probes are able to differentiate groups of CTV strains which are not distinguishable from each other by other methods. The probes were completely specific, i.e. reacting only with extracts of plants infected with the CTV strains to which they were prepared and not with other strains or with extracts of healthy plants. These probes can detect as little as 1.0 ng of target CTV DNA (0.5 ng of actual target molecule). Therefore, they are very specific and sensitive. The specificity of probes depends on as few as 1–2 common nucleotide changes in specific position of the CPG of the isolates in the same group. Since the probes are labeled with biotin, they are safe and can be stored and used for an extended period of time.

Differences as small as a single nucleotide in the CPG sequences are useful for differentiating symptom severity of CTV strains which cannot easily be differentiated by other methods. This also indicates that such minor sequence differences in any part of the CTV genome can potentially be used to differentiate important CTV strains. Thus, the development of probes for known groups or individual strains of CTV can be used for rapid identification and classification of newly discovered CTV isolates.

In a method according to the subject invention, viral genetic material is extracted, transcribed if required, and subjected to conventional hybridization procedures using a probe of the subject invention. Typically, a sample is taken from a host plant suspected of harboring CTV. The CTV, or tissue containing CTV, is extracted from the host plant or tissue sample according to known procedures. Genetic material from the host or CTV is then isolated using techniques known in the art. Since CTV is an RNA virus, its genetic message can be conveniently converted to DNA as a part of the amplification process. Amplification by reverse transcriptase/polymerase chain reaction procedures (RT/PCR), employing the primers CN119 (SEQ. ID. NO. 10) and CN120 (SEQ. ID. NO. 11) disclosed herein, can be performed on the isolated genetic material to make DNA copies of the capsid protein encoding sequences from the viral strains. The primers used, CN119 and CN120, are not strain specific. Finally, hybridization and detection steps can be carried out as described herein using a labeled probe of the subject invention in conventional hybridization and detection procedures.

In an alternative embodiment, nucleic acid isolated from CTV can be tested for the ability to bind to immobilized probe (e.g., those corresponding to SEQ ID Nos:1–9). For example, for PCR ELISA, the oligonucleotide probes can be immobilized on the bottom portions of the wells in a ninety-six well polystyrene microtiter plate. Immobilization of the probes can be performed by adapting known techniques, e.g., by first coating the wells with streptavidin and then adding biotin-labeled probes to the wells under conditions that allow the biotin to bind to the streptavidin. Immobilization of the probes for PCR ELISA can also be performed by unconventional techniques. For example, rather than having to biotinylate the probe(s), the probes can be directly cross-linked to the substrate. Any agent suitable for cross-linking a nucleic acid to the material comprising the substrate can be used. Numerous cross-linking agents are commercially available from, e.g., Pierce (Rockford, Ill.) and Sigma (St. Louis, Mo.). For example, when the substrate is polystyrene, a suitable cross-linking agent is EDAC (1-Ethyl-3-(3-Dimethylamino-Propyl) Carbodiimide-HCl; Sigma, St. Louis. MO). Once the probe(s) have been immobilized on the substrate, a test sample including a nucleic acid can be added to the immobilized probe to assess its ability to bind the probe.

For example, to test the ability of test samples containing a nucleic acid encoding all or part of a CTV capsid protein gene, the nucleic acid can be amplified using PCR (e.g, asymmetric PCR) using the primers of SEQ ID NOs: 10 (CN119) and II (CN120). The PCR reaction products can then be added to the immobilized probe(s), and binding between the probe and the PCR products assessed. To detect such binding, the PCR products can be conjugated with a detectable label (e.g., biotin, a chromogenic agent, a fluorescent agent, a chemiluminescent agent, a radioactive tag, etc.). Any detectable label compatible with the particular assay can be used. In a preferred variation, the label is digoxygenin. Digoxygenin-labeled nucleic acids can be detected using digoxygenin specific antibodies that are conjugated with a detectable label (e.g., an enzyme such as alkaline phosphatase or horseradish peroxidase).

A newly discovered CTV strain can also be identified by employing the probes and methods described in the invention. First, the newly discovered isolates can be tested by the universal probe (Probe 0) to determine if it can be identified as CTV. If so, Probe VIII can be used to determine if it is a mixture of mild strains. Alternatively or additionally, Probes I–VII can further be used to characterize the particular severe or mild strain by blot, dot-blot, or other conventional means of hybridization. Finally, if a new isolate does not hybridize with any of the group specific probes, its CPG can be cloned and sequenced in accordance with the procedures known or described herein. Using the CPG sequences, the relationships between that new isolate and known strains of CTV can be determined. Pursuant to the teachings provided for the subject invention, a specific probe can be designed to hybridize to its unique sequence in order to detect that new strain in other hosts.

In addition, the subject invention includes a kit for carrying out the subject detection or identification methods. The kit can include one or more of the subject probes (Probes I–VIII or Probe 0) for various levels of detection specificity. Other materials useful for performing the subject method can also be included as part of the kit. For example, the kit can include buffers or labware necessary to obtain or store samples from a host, or isolate or purify target genetic material from the host. Further, the kit can include materials (e.g., chemicals or buffers) or labware for performing hybridization and detection procedures. The kit can also include labeling materials for labeling the probes. Written materials describing the steps involved in the subject method can be included for instructing the user how to use the article of manufacture or kit.

It is specifically intended that other nucleic acid testing procedures can be used to test for RNA or DNA (made from viral RNA) which is associated with a level of viral symptom severity. For example, enzyme-based assays are possible based on nucleic acid hybridizations to the targeted sequences. What is important here is that the targeted or diagnostic sequences are associated with a common level of symptom severity in strains harboring that sequence.

EXAMPLES

The present invention is further illustrated by the following specific examples. The examples are provided for illustration only and are not to be construed as limiting the scope or content of the invention in any way. All percentages are by weight and all solvent mixture proportions are by volume unless otherwise noted.

Example 1

Detection of CTV Strains by Blot Hybridization

Two isolates from each of Groups I–VII (see Table 1 above) were tested by blot hybridization. The representative isolates of each group were obtained from the Collection of Exotic Citrus Pathogens in Beltsville, Md. Crude nucleic acids, extraction, and polymerase chain reaction (PCR) amplification of CPG, as well as the analysis of the PCR amplification product were performed using technologies well known and readily available to those of ordinary skill in the art.

The amplified CPGs of 14 CTV isolates were electrophoresed in 1% agarose gel. The DNA in the gel was first denatured by incubating the gel in a denaturing solution of 1.5 M NaCl and 0.5 M NaOH for 1–1.5 hr at room temperature with gentle agitation. The neutralizing solution (1–5 M NaCl and 0.5 M Tris-Ci pH 8.0) was then applied to the gel at room temperature for 1–1.5 hr with gentle agitation. The DNAs were then capillary transferred, as described Sambrook et al., 1989, to GeneScreen Plus membrane (DuPont), a positively charged nylon membrane. When the transfer was completed, the DNA was fixed to the membrane by UV crosslinking in a UV Stratalinker 1800 (Stratagene), and the membrane was kept in the dark at room temperature until used.

Prehybridization of the membrane was performed for all probes at 37° C. for 1–1.5 hr in a hybridization bag containing 0.1 ml of prehybridization solution per $cm^2$ of membrane. The prehybridization solution consisted of 5× sodium saline citrate (SSC) (1×SSC is 0.15 M NaCl and 0.015 M sodium citrate, pH 7.0), 5× Denhardt's solution, 1% SDS, 0.01 M phosphate buffer ($NaPO_4$ pH 6.8), 1 mM adenosine 5'-phosphate (ATP), and 1 mM EDTA. 0.2 mg salmon sperm DNA per ml of prehybridization solution was added into the hybridization bag.

After 1–1.5 hr prehybridization, 50 ng of the biotin-labeled group specific oligonucleotide probe was added into the prehybridization solution and hybridized overnight at 37° C. with gentle agitation. When the hybridizations were completed, the probes were frozen at −20° C. for further use. The membrane was washed twice with 6×SSC at room temperature with gentle agitation and then washed with gentle agitation in 6×SSC and 0.1% SDS at 37° C. Since the homology between the target DNA on the membrane and the specific probe was nearly 100%, a stringent wash with 6×SSC and 1% SDS was performed at 42° C. to remove the non-specifically bound probes. A more stringent wash at 42° C. with 4×SSC and 1% SDS was used for probes I, II, III and V, which have a melting temperature of 50° C. or higher.

The conjugate used for detection was streptavidin-horseradish peroxidase (SA-HRP) diluted 1:1000 in 1.5% BSA in TBS-T buffer. To prevent the non-specific bindings of the SA-HRP conjugate, the membrane was first incubated in 3% BSA in TBS-T buffer at room temperature with gentle agitation. The membrane was then incubated in a container with 0.1 ml of SA-HRP diluted in TBS-T per $cm^2$ of membrane at room temperature with gentle agitation for 1 hr. The membrane was rinsed five times with TBS-T at room temperature with gentle agitation for at least 5 minutes each rinse. The number of washes was very important to remove excess SA-HRP conjugate to decrease background.

SuperSignal CL-HRP substrate system (Pierce Inc., Rockford, Ill.), a chemiluminescence substrate, was used for the detection of the HRP labeled SA-biotin complex. Equal volume of the two components of the detection system, 2× Luminol/enhancer solution and 2× stable peroxide solution, were mixed and diluted 1:2 in $ddH_2O$. The substrate mixture was applied to the membrane for 3–5 min at RT. The membrane was then removed from the substrate solution and placed in plastic wrap and exposed to X-ray film.

The probe hybridized to the target DNA on the membrane was completely removed by incubating the membrane first in 0.4 N NaOH at 42° C. for 30 minutes, and then in a solution containing 0.2 M Tris-Cl, 0.1× SSC and 0.1% SDS at 42° C. for 30 minutes. The membrane was rinsed in 10× SSC, prehybridized and hybridized with another probe. The same membrane was re-probed up to ten times. Thus, a single membrane can be tested with a number of probes without any loss of signal.

(A) Probe I. Fourteen (14) biologically and geographically different CTV isolates were amplified using RT/PCR and hybridized with Probe I. Specifically, the isolates were: T36 and T66 of Group I; B1 and B53 of Group II; B165 and B185 of Group III; T3 and B220 of Group IV; B128 and B249 of Group V; T26 and T30 of Group VI; and B188 and B215 of Group VII. The DNA from each isolate was electrophoresed on a single agarose gel along with a 100 bp DNA size marker and the RT/PCR amplification product from healthy citrus tissue as a negative control. Probe I hybridized only with T36 and T66, the isolates of Group I, and not with the CPG from any other of the groups of isolates.

(B) Probe II. DNA from the fourteen (14) CTV isolates, as described in Example 3(A) above, were hybridized with Probe II. Probe II hybridized with B53 and B1, the isolates of Group II. Hybridization was very strong with B53 but weak with B1. The weak reaction was not due to a lower concentration of DNA in the membrane, because the amount of B1 in the membrane was equal to or greater than the DNA of isolate B53. No other isolates reacted with Probe II.

(C) Probe III. Hybridization of fourteen (14) CTV isolates, as described in Example 3(A) above, was carried out using Probe III. Probe III hybridized only with B165 and B185, the two isolates of CTV Group III.

(D) Probe IV. Hybridization of fourteen (14) CTV isolates, as described in Example 3(A) above, was carried out using Probe IV. Hybridization of Probe IV revealed positive reactions only with T3 and B220, the two representative isolates from Group IV.

(E) Probe V. Hybridization of fourteen (14) CTV isolates, as described in Example 3(A) above, was carried out using Probe V. With Probe V, hybridization occurred with both B1128 and B249, the representative isolates of Group V. However, Probe V also hybridized with B1, which is in Group II. The reaction was very strong, even stronger than its reaction with B128 and B249, even after several stringent washes. With B1, the intensity of the band by hybridization with Probe II was much weaker than with Probe V. This indicates that B1, indeed possesses sequences specific to both isolate Groups II and V. The tree from which B1 was isolated was found to be infected with two strains differing in their concentrations, with the one having the Probe V sequence in higher concentration.

(F) Probe VI. Hybridization of fourteen (14) CTV isolates, as described in Example 3(A) above, was carried out using Probe VI. Probe VI hybridized with Group VI isolates T26 and T30 from Florida, but not with CPGs of any other mild or severe strain of CTV present in the membrane.

(G) Probe VII. Hybridization of fourteen (14) CTV isolates, as described in Example 3(A) above, was carried out using Probe VII. Probe VII hybridized only with two oriental mild strains, B188 and B215, from Group VII. A very weak reaction occurred with T30, but stringent washes eliminated that hybridization. There was no reaction with T26 which has the same sequence as T30 in the Probe VII region. Thus, this non specific hybridization was caused by the relatively high amount of T30 CPG DNA present in the membrane.

(H) Probe VIII. Hybridization of fourteen (14) CTV isolates, as described in Example 3(A) above, was carried out using Probe VIII. Probe VIII, which can differentiate between mild and severe strains of CTV, reacted with all mild strains present in the membrane, but did not react with any of the severe strains.

(I) Probe 0. Hybridization of fourteen (14) CTV isolates, as described in Example 3(A) above, was carried out using Probe 0. Finally, Probe 0, the "universal" probe, hybridized with all fourteen (14) strains of CTV tested regardless of the origins or biologically characteristics of the strain. The reaction was very strong under both low and high stringency conditions.

In order to determine the sensitivity of the biotin labeled oligonucleotide probes, the RT/PCR amplification product of T36 was purified by the Wizard DNA column (Promega). The concentration was determined by spectrophotometry. Different amounts (1 $\mu$g, 100 ng, 50 ng, 10 ng, 1 ng, 100 pg, 10 pg and 1 pg) of DNA were separated in a 1% agarose gel and transferred to a nylon membrane. The membrane was probed with Probe I. Hybridization of Probe I with the target CTV CPG DNA was detectable up to the 1 ng level. The washing at low stringency and increased exposure time affected the intensity of the bands observed, but did not change the sensitivity.

Example 2

Detection Of CTV Strains by PCR ELISA

CTV strains in Groups I–VII were obtained from the Collection of Exotic Citrus Pathogens and tested by PCR ELISA. The following buffers and reagents were used in this process were prepared as described below. The pH of each was adjusted with NaOH or HCl as appropriate. ELISA coating buffer was made by dissolving $Na_2CO$ (1.59 g/l) and $NaHCO_3$ (2.93 g/l) in water, and adjusting the solution to pH 9.6. PBS was made by dissolving NaCl (8 $\mu$l), $KH_2PO_4$ (0.24 g/l), $Na_2HPO_4$ (1.44 g/l), and KCl (0.2 $\mu$l) in water, and adjusting the solution to pH 7.4. PBST was made by adding 0.5 ml Tween 20 per liter of PBS. Hybridization buffer was made by dissolving 5× SSPE, 0.1% n-lauroylsarcosine, 0.5M NaCl in water, and adjusting the solution to pH 6.5. 20× SSPE was made by dissolving NaCl (175.3 g), $NaH_2PO_4$—$H_2O$ (27.6 g), EDTA (7.4 g or 40 ml of 500 mM stock) in 800 ml of deionized water; then adjusting the solution to pH 7.4 with NaOH; and finally adjusting the volume to one liter with deionized water. ELISA substrate buffer was made by dissolving 97 ml of diethanolamine into 800 ml of deionized water, adjusting the pH of the solution to 9.8 with concentrated HCl, and finally adjusting the volume to one liter with deionized water.

Microtiter plates for PCR ELISA were prepared by immobilizing the oligonucleotide probes (e.g., the oligonucleotides corresponding to SEQ ID NOs: 1–9) on the bottom portions of the wells in a ninety-six well polystyrene microtiter plates. Specifically, 100 ul of a solution including 0.2 mM of the oligonucleotide probe in 20 mM EDAC (1-Ethyl-3-(3-Dimethylamino-Propyl) Carbodiimide-HCl; Sigma, St. Louis. MO) was added to the wells in the microtiter plate, and the plate was incubated overnight at room temperature to allow the probes to bind the well bottoms. The plate was divided such that some wells contained only probe corresponding to one of SEQ ID NOs: 1–9. After the overnight incubation, the EDAC/probe solutions were discarded by forcefully shaking the solutions out of the plates. The plates were then washed three times with PBS-T from a wash bottle, with 3 min between washes. In some cases the plates were allowed to air dry following the last wash with PBS-T. Such plates were stored at 4° C. for up to one month with no loss of activity.

Using the PCR primers of SEQ ID Nos: 10 (CN119) and II (CN120), the CPG portions of the CTV genome of each isolate tested were amplified using asymetrical PCR. Primers CN 119 and CN 120 were used at 10 uM and 1 uM, repectively, in order to preferentially amplify the positive (or mesage) strand of the CTV CPG (i.e., the strand that the probes corresponding to SEQ ID NOs: 1–9 were designed to hybridize to). The DNA was labeled during the PCR reaction by the incorporation of digoxygenin-labeled UTP into the DNA in place of TTP. For each test sample, 5 ul of each PCR reaction product solution (adding more produced a faster reaction) was added to a corresponding well in the microtiter plate. Ninety-five ul of hybridization buffer was added to the wells to bring the final volume in each well to 100 ul. The plate was then incubated at 37° C. for 90 minutes to allow the PCR products to bind to the immobilized probes. The plates were then washed 3 times with PBS-T (as described above) to remove unbound PCR reaction products.

To detect bound PCR reaction products, 100 ul/well of anti-DIG-Fab fragment conjugated to alkaline phosphatase diluted 1:1,000 (from a stock of 150 units/200 ul, Roche Catalog No. 1093274) in PBS-T. The plates were then incubated at 37° C. for 30 minutes, after which time, the plates were then washed 3 times with PBS-T (as described above) to remove unbound anti-DIG-Fab fragments. The presence of the anti-DIG-Fab fragments was detected using a p-nitrophenyl phosphate substrate, which was prepared by dissolving 3×5 mg tablets of p-nitrophenyl phosphate (Sigma) in 20 ml of ELISA substrate buffer (alternatively a 0.75 mg/ml solution of pure substrate can be prepared). One hundred ul of the substrate solution was added to each well, and the plate was incubated at room temperature until color development (usually about 1 hour). The plate was then read using an ELISA plate reader at 405 nm. Data obtained using this system showed that it can be used to identify and differentiate among stains of CTV.

Other Embodiments

This description has been by way of example of how the compositions and methods of invention can be made and carried out. Those of ordinary skill in the art will recognize that various details may be modified in arriving at the other detailed embodiments, and that many of these embodiments will come within the scope of the invention.

Therefore, to apprise the public of the scope of the invention and the embodiments covered by the invention, the following claims are made.

What is claimed is:

1. A method comprising the steps of:
   contacting a test sample with a probe comprising an oligonucleotide selected from the group consisting of SEQ ID NOS: 1–8 and the complements of SEQ ID NOS: 1–8; and
   analyzing binding of the probe to the test sample.

2. The method of claim 1, further comprising the step of: isolating nucleic acid from the test sample.

3. The method of claim 2, further comprising the step of: amplifying the nucleic acid isolated from the test sample using polymerase chain reaction.

4. The method of claim 3, wherein the amplifying step comprises the step of adding a first oligonucleotide primer and a second oligonucleotide primer to the nucleic acid isolated from the test sample, the first and second oligonucleotide primers together capable of selectively mediating amplification of a polynucleotide derived from a Citrus Tristeza Virus to which the oligonucleotide probe can hybridize.

5. The method of claim 4, wherein the first oligonucleotide primer consists essentially of SEQ ID NO:10, and the second oligonucleotide primer consists essentially if SEQ ID NO:11.

6. The method of claim 1, wherein said oligonucleotide probe comprises a nucleic acid molecule selected from the group consisting of: SEQ ID NO:1, SEQ ID NO:2, SEQ ID NO:3, SEQ ID NO:4, SEQ ID NO:5, SEQ ID NO:6, SEQ ID NO:7, and SEQ ID NO:8.

* * * * *

SEQUENCE LISTING

```
<160> NUMBER OF SEQ ID NOS: 11

<210> SEQ ID NO 1
<211> LENGTH: 18
<212> TYPE: DNA
<213> ORGANISM: Artificial Sequence
<220> FEATURE:
<221> NAME/KEY: misc_feature
<223> OTHER INFORMATION: nucleic acid probe that hybridizes to Group I
      CTV strains

<400> SEQUENCE: 1
gaaataccgc acacaagt                                                   18

<210> SEQ ID NO 2
<211> LENGTH: 17
<212> TYPE: DNA
<213> ORGANISM: Artificial Sequence
<220> FEATURE:
<221> NAME/KEY: misc_feature
<223> OTHER INFORMATION: nucleic acid probe that hybridizes to Group II
      CTV strains

<400> SEQUENCE: 2
tgacgcacgt cattcat                                                    17

<210> SEQ ID NO 3
<211> LENGTH: 15
<212> TYPE: DNA
<213> ORGANISM: Artificial Sequence
<220> FEATURE:
<221> NAME/KEY: misc_feature
<223> OTHER INFORMATION: nucleic acid probe that hybridizes to Group III
      CTV strains

<400> SEQUENCE: 3
ccacttcgac gccct                                                      15

<210> SEQ ID NO 4
<211> LENGTH: 17
<212> TYPE: DNA
<213> ORGANISM: Artificial Sequence
<220> FEATURE:
<221> NAME/KEY: misc_feature
<223> OTHER INFORMATION: nucleic acid probe that hybridizes to Group IV
      CTV strains

<400> SEQUENCE: 4
tcccgagtat atgttat                                                    17

<210> SEQ ID NO 5
<211> LENGTH: 19
<212> TYPE: DNA
<213> ORGANISM: Artificial Sequence
<220> FEATURE:
<221> NAME/KEY: misc_feature
```

```
<223> OTHER INFORMATION: nucleic acid probe that hybridizes to Group V
      CTV strains

<400> SEQUENCE: 5
acacccgtgg tatcatcgt                                              19

<210> SEQ ID NO 6
<211> LENGTH: 15
<212> TYPE: DNA
<213> ORGANISM: Artificial Sequence
<220> FEATURE:
<221> NAME/KEY: misc_feature
<223> OTHER INFORMATION: nucleic acid probe that hybridizes to Group VI
      CTV strains

<400> SEQUENCE: 6
ccgctaatcg gtata                                                  15

<210> SEQ ID NO 7
<211> LENGTH: 17
<212> TYPE: DNA
<213> ORGANISM: Artificial Sequence
<220> FEATURE:
<221> NAME/KEY: misc_feature
<223> OTHER INFORMATION: nucleic acid probe that hybridizes to Group VII
      CTV strains

<400> SEQUENCE: 7
ctgcacacag ataatga                                                17

<210> SEQ ID NO 8
<211> LENGTH: 17
<212> TYPE: DNA
<213> ORGANISM: Artificial Sequence
<220> FEATURE:
<221> NAME/KEY: misc_feature
<223> OTHER INFORMATION: nucleic acid probe that hybridizes to CTV mild
      strains

<400> SEQUENCE: 8
ttatacacga tgtcggt                                                17

<210> SEQ ID NO 9
<211> LENGTH: 14
<212> TYPE: DNA
<213> ORGANISM: Artificial Sequence
<220> FEATURE:
<221> NAME/KEY: misc_feature
<223> OTHER INFORMATION: nucleic acid probe that hybridizes to all CTV
      strains

<400> SEQUENCE: 9
ggatcgatgt gtaa                                                   14

<210> SEQ ID NO 10
<211> LENGTH: 27
<212> TYPE: DNA
<213> ORGANISM: Artificial Sequence
<220> FEATURE:
<221> NAME/KEY: misc_feature
<223> OTHER INFORMATION: oligonucleotide primer for PCR amplification of
      CTV CPG

<400> SEQUENCE: 10
agatctacca tggacgacga aacaaag                                     27

<210> SEQ ID NO 11
```

```
<211> LENGTH: 27
<212> TYPE: DNA
<213> ORGANISM: Artificial Sequence
<220> FEATURE:
<221> NAME/KEY: misc_feature
<223> OTHER INFORMATION: oligonucleotide primer for PCR amplification of
      CTV CPG

<400> SEQUENCE: 11
gaattcgcgg ccgctcaacg tgtgtta                                              27
```